United States Patent [19]

Tanabe et al.

[11] Patent Number: 4,841,981
[45] Date of Patent: Jun. 27, 1989

[54] CATHETERS FOR MEASUREMENT OF CARDIAC OUTPUT AND BLOOD FLOW VELOCITY

[75] Inventors: Susumu Tanabe; Shigekazu Sekii; Kouji Tsuchida; Yoshio Ishizu, all of Fujinomiya, Japan

[73] Assignee: Terumo Corporation, Tokyo, Japan

[21] Appl. No.: 21,912

[22] Filed: Mar. 4, 1987

[30] Foreign Application Priority Data

Mar. 7, 1986 [JP] Japan .................................. 61-48681

[51] Int. Cl.$^4$ .............................................. A61B 5/02
[52] U.S. Cl. .................................. 128/692; 128/713; 128/736
[58] Field of Search ............................... 128/691-693, 128/713, 736; 73/204

[56] References Cited

U.S. PATENT DOCUMENTS

| | | | |
|---|---|---|---|
| 3,438,253 | 4/1969 | Kuether et al. | 73/204 |
| 3,595,079 | 7/1971 | Grahn | 73/204 |
| 3,678,922 | 7/1972 | Phillips . | |
| 3,789,831 | 2/1974 | Kopaniky et al. . | |
| 3,820,530 | 6/1984 | Gilford et al. . | |
| 3,995,623 | 12/1976 | Blake et al. . | |
| 4,004,576 | 1/1977 | Gahwiler et al. . | |
| 4,035,622 | 7/1977 | Obermajer . | |
| 4,230,126 | 10/1980 | Elings | 128/671 |
| 4,240,441 | 12/1980 | Khalil | 128/692 |
| 4,380,237 | 4/1983 | Newbower | 128/693 |
| 4,502,488 | 3/1985 | Degironimo et al. | 128/692 |
| 4,542,748 | 9/1985 | Roy | 128/736 X |
| 4,572,206 | 2/1986 | Geddes et al. | 128/692 |
| 4,595,015 | 6/1986 | Jansen et al. | 128/692 X |
| 4,621,646 | 11/1986 | Bryant | 128/692 |
| 4,632,125 | 12/1986 | Webler et al. | 128/692 |
| 4,685,470 | 8/1987 | Sekii | 128/692 |

FOREIGN PATENT DOCUMENTS 0182363 5/1986 European Pat. Off. .
WOA8403431 9/1984 World Int. Prop. O. .

OTHER PUBLICATIONS

Medical and Biological Engineering, vol. 11, No. 2, Mar. 1973, pp. 201-205; (Stevenage, Herts, GB) A. L. Delaunois: "Thermal Method for Continuous Blood-Velocity Measurements in Large Blood Vessels, and Cardiac-Output Determination."

Robert B. Dew, "Personal Computer System For Automatic Coronary Venous Flow Measurement", *Computer Applications in Medical Care*, Proceedings, The Ninth Annual Symposium, Nov. 10-13, 1985, Baltimore, MD.

European Search Report, EP 87 10 3083 on Apr. 13, 1988 at the Hague by Examiner A. Ferrigno.

*Primary Examiner*—Kyle L. Howell
*Assistant Examiner*—Angela D. Sykes
*Attorney, Agent, or Firm*—Staas & Halsey

[57] ABSTRACT

A catheter introduced into the pulmonary artery for use in measuring cardiac output or blood flow velocity includes temperature sensing device including a temperature sensing element for sensing the temperature of blood in the pulmonary artery diluted by an indicator liquid infused for measurement of cardiac output based on a thermodilution method, and a self-heating thermistor for sensing a signal relating to blood flow velocity near the temperature sensing element, the signal being an equilibrium temperature sensed by the thermistor. The catheter is connected to a cardiac output measurement system adapted to measure cardiac output on the basis of the thermodilution method, measure the blood flow velocity which prevails when the cardiac output is measured, and obtain a parameter which links this blood flow velocity to the cardiac output measured in accordance with the thermodilution method. Once the parameter is found, merely measuring the blood flow velocity enables cardiac output to be determined from the flow velocity and the parameter.

5 Claims, 9 Drawing Sheets

CATHETERS FOR MEASUREMENT OF CARDIAC OUTPUT AND BLOOD FLOW VELOCITY

RELATED APPLICATIONS

Patent applications directly or indirectly related to the subject application are the following:

Japanese Patent Application No. 59-244586 (filed on Nov. 21, 1984 and laid open on June 13, 1986 as Japanese Patent Application Laid-Open No. 61-125329;

European Patent Application No. 85114716.5 (filed on Nov. 19, 1985 and published on May 28, 1986 as No. 0182363) based upon the Japanese Patent Application No. 59-244586. U.S. Pat. No. 4,685,470, also based upon Japanese Patent Application No. 59-244586.

BACKGROUND OF THE INVENTION

1. Field of the Invention

This invention relates to a catheter for measuring cardiac output, and to a cathether for measuring blood flow velocity, which are connected to a cardiac output measurement system used in examining cardiac function.

2. Description of the Prior Art

In order to measure cardiac output by the right heart catheter method for the purpose of examining cardiac function, the conventional practice is to employ an indicator dilution method. Thermodilution, which is one of the indicator dilution methods available, will now be described with reference to FIGS. 5 and 6.

Figure 5:
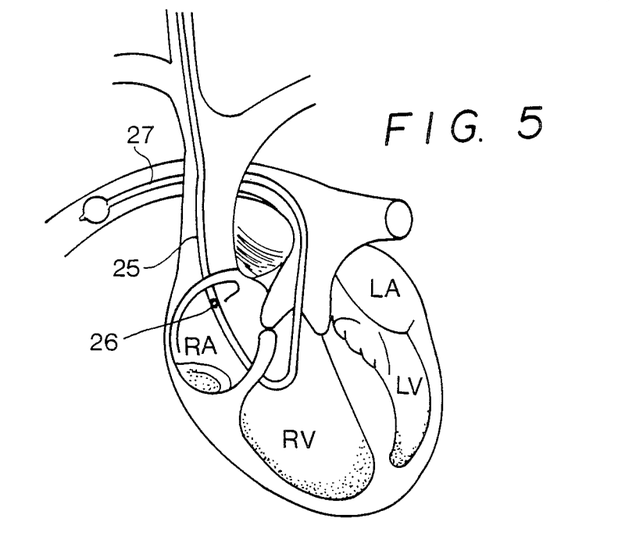
FIG. 5 is a view useful in describing an example of arranging a catheter in accordance with the right heart catheter method.
Figure 6:
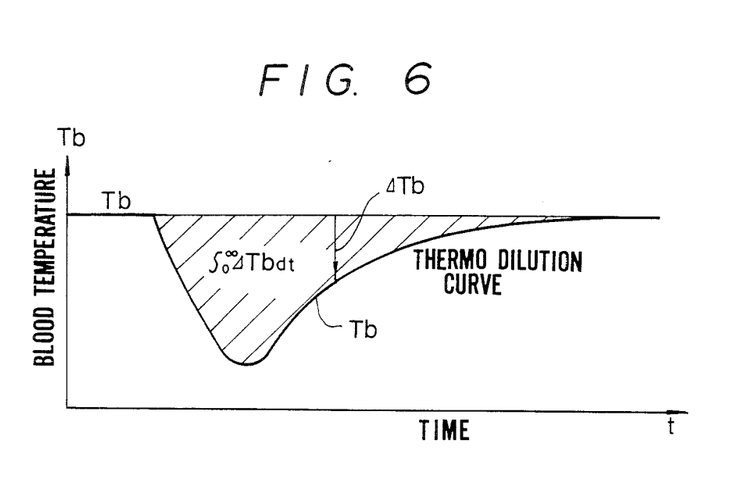
FIG. 6 is a thermodilution curve expressing a change in blood temperature with time due to introduction of a injectate liquid.

According to the right heart catheter method, a catheter 4 is introduced from a jugular vein, femoral vein or elbow vein and is passed through the ascending or descending vena cava, the right auricle RA and the right ventricle RV to position its distal end in the pulmonary artery. The catheter 4 includes a discharge port 3 and a thermistor 1 and is so adapted that the discharge port 3 and thermistor 1 occupy positions in the right auricle RA and pulmonary artery, respectively. With the catheter 4 so disposed, a liquid the temperature whereof is higher or lower than blood temperature is introduced into the right auricle RA from the discharge port 3, whereupon the liquid spreads and is diluted in the right auricle RA and right ventricle RV. The temperature of the diluted liquid is sensed by the thermistor 1 situated in the pulmonary artery, allowing cardiac output to be calculated from the area of the thermal dilution curve (change in temperature with time, as shown in FIG. 6) in accordance with the following Eq. (1), developed by Stewart Hamilton:

$$CO = \frac{S_i \cdot C_i \cdot (T_b - T_i) \cdot V_i}{S_b \cdot C_b \cdot \int_0^\infty \Delta T_b dt}$$

where
CO: cardiac output,
$S_i$ specific gravity of injectate liquid,
$C_i$ specific heat of injectate liquid,
$V_i$ amount of injectate liquid,
$T_i$ temperature of injectate liquid,
$T_b$ temperature of blood,
$S_b$ specific gravity of blood,
$C_b$ specific heat of blood, $\int_0^\infty \Delta T_b dt$: area of thermal dilution curve A disadvantage of the conventional cardiac output measurement system which relies upon an indicator dilution method such as the above-described thermodilution method is that measurement of cardiac output is performed intermittently and not continuously. Moreover, when it is attempted to perform measurement frequently, the total amount of injectate liquid assumes large proportions, thereby submitting the patient to a considerable burden. Another problem is that the liquid injection operation is accompanied by increased risk of infection.

SUMMARY OF THE INVENTION

Accordingly, an object of the invention is to provide a cardiac output measurement catheter well suited for collecting information or signals necessary for a cardiac output measurement system capable of performing a cardiac output measurement continuously with less burden upon the patient and with reduced risk of infection.

Another object of the invention is to provide a blood flow velocity measurement catheter well suited for collecting information or signals necessary for the abovementioned cardiac output measurement system.

The catheter for measuring cardiac output or blood flow velocity in accordance with the invention is connected to a cardiac output measurement system. The latter is adapted to measure cardiac output on the basis of a dilution method such as a thermodilution method, resistance value dilution method or dye dilution method, measure blood flow velocity which prevails when the cardiac output is measured, and obtain a parameter which links this blood flow velocity to the cardiac output measured in accordance with the dilution method. Once the parameter has been found, it will suffice thenceforth merely to measure the blood flow velocity to enable cardiac output to be determined from the flow velocity and the parameter.

Accordingly, the catheter for measuring blood flow velocity in accordance with the present invention comprises temperature sensing element for sensing blood temperature, and a heating element for heating the temperature sensing element, wherein the temperature sensing element measures an equilibrium temperature resulting from the quantity of heat applied by the heating element and the quantity of heat absorbed by the blood, and produces an output signal indicative of the equilibrium temperature.

In accordance with a preferred embodiment of the invention, the heat sensing element and heating element construct an integrated self-heating type thermistor.

The catheter for measuring cardiac output in accordance with the present invention comprises an aperture portion for discharging an indicator liquid for dilution purposes in a dilution method, and blood flow velocity signal detecting means for outputting information or signals necessary for measuring blood flow velocity. The indicator liquid is one containing a predetermined dye if the dilution method employed is the dye dilution method, and one containing a predetermined electrolytic medium if the dilution method is the resistance value dilution method.

In a preferred embodiment of the invention, the blood flow velocity signal detecting means comprises a temperature sensing element for sensing blood temperature, and a heating element for heating the temperature sensing element, wherein the temperature sensing element measures an equilibrium temperature resulting from the quantity of heat applied by the heating element and the quantity of heat absorbed by the blood, and produces an output signal indicative of the equilibrium temperature.

The catheter for measuring cardiac output in accordance with another aspect of the present invention comprises an aperture portion for discharging an indicator liquid for dilution purposes in a dilution method, temperature sensing means for sensing the temperature of blood diluted by the liquid discharged from the aperture portion, and for producing an output signal indicative of the sensed temperature, and blood flow velocity signal detecting means for detecting information or signals necessary for measuring blood flow velocity.

In a preferred embodiment of the invention, the blood flow velocity signal detecting means comprises a temperature sensing element for sensing blood temperature, and a heating element for heating the temperature sensing element, wherein the temperature sensing element measures an equilibrium temperature resulting from the quantity of heat applied by the heating element and the quantity of heat absorbed by the blood, and produces an output signal indicative of the equilibrium temperature.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Figure 1:
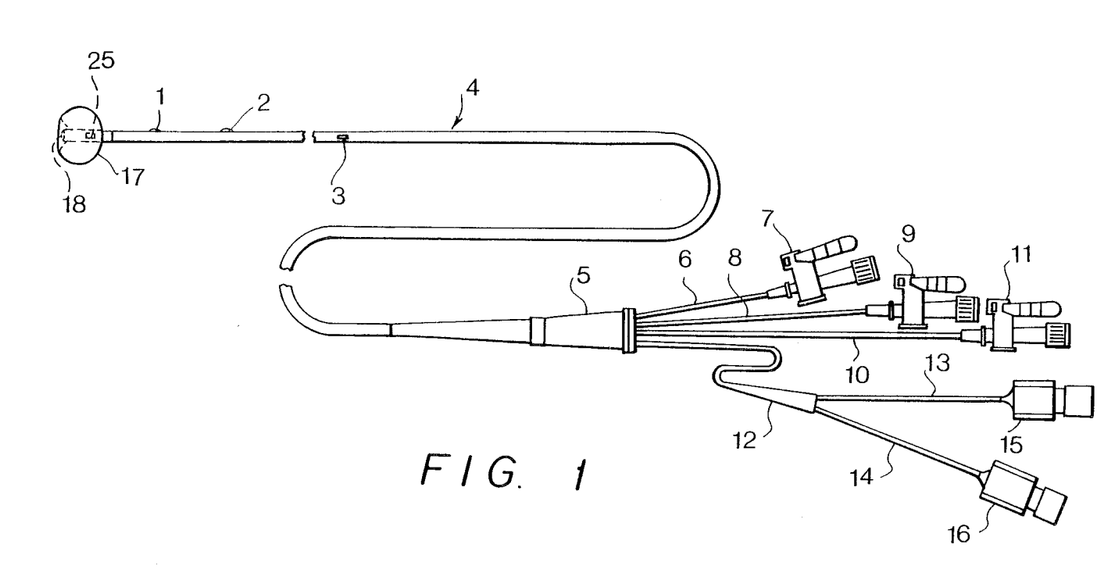
FIG. 1 is an overall perspective view illustrating an embodiment of a catheter for measuring cardiac output in accordance with the present invention.
Figure 2:
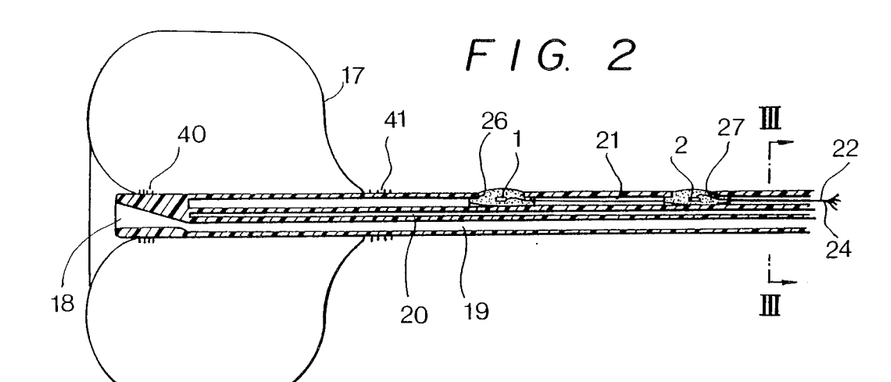
FIG. 2 is an enlarged sectional view illustrating a principal portion of the catheter shown in FIG. 1.

A typical embodiment of a catheter according to the present invention is constructed as shown in FIGS. 1 and 2. The catheter is connected to a cardiac output measurement system or blood flow velocity measurement system which operates in cooperation with the catheter. The catheter is adapted to supply the particular system with information or signals necessary for the cardiac output or blood flow velocity measurement, whereby the system is capable of measuring cardiac output or blood flow velocity continuously. The construction of the catheter will be described first, followed by a discussion of system operation. If the catheter is used in continuous measurement of cardiac output, the measurement system measures cardiac output based on the dilution method, and a parameter is found linking the measured cardiac output and a blood flow velocity corresponding to this cardiac output. Accordingly, a cathether used solely for measuring blood flow velocity will be self-evident from the description of the catheter used in measuring cardiac output.

With reference to FIG. 1, a catheter 4 in accordance with the invention is constructed to have four lumens, described below. The catheter 4 includes a pressure sensing port 18 provided its tip, a balloon 17 comprising a flexible elastic body attached to the catheter tube at a position several millimeters from the tip thereof so as to cover the entirety of the tip portion of the catheter tube, a hole 25 provided in the side of the catheter tube within the balloon 17 for the purpose of introducing and venting air to inflate and deflate the balloon 17, a thermistor 1 provided on the catheter tube at a position 10 to 20 mm from the tip thereof, a thermistor 2 provided on the catheter tube at a position 10 –15 mm from the thermistor 1 on the side facing the base end of the catheter, and a discharge port 3 provided in the catheter tube at a position 8.5–38 cm from the thermistors 1, 2 and 12–40 cm from the tip of the catheter. The thermistor 1 is used to measure equilibrium temperature for the purpose of measuring blood flow velocity. The thermistor 2 is used to measure the temperature of diluted blood necessary for measuring cardiac output in accordance with the thermodilution method.

The catheter shown in FIG. 1 is introduced into the jugular vein, femoral vein or elbow vein and passed through the ascending or descending vena cava, the right atrium and right ventricle and used in the pulmonary artery. Therefore, in view of the fact that the blood flows from the base end side of the catheter toward the distal end side thereof, the thermistor 2 is provided on the distal end side of the discharge port 3 (i.e. on the side downstream of the blood flow). In a case where the catheter is introduced into a peripheral artery and used in a main artery on the other hand, the blood flows in the opposite direction; hence, the thermistor 2 would be arranged on the base end side of the discharge port 3.

FIG. 2 is a sectional view showing the principal portion of the catheter 4. The pressure sensing port 18, the hole 25 for the balloon, the thermistors 1, 2 and the discharge port 3 communicate with respective ones of the four lumens. These are a pulmonary arterial pressure lumen 19 for transmitting the pressure prevailing in the pulmonary artery, a balloon lumen 20 constituting an air passageway for inflating and deflating the balloon 17, a thermistor lumen 21 accommodating thermistors 1, 2 and their lead wires, and an infusion lumen 23 through which a diluting indicator liquid is passed for use in accordance with the thermodilution method. These four lumens are independent of one another and are connected to a tube 8 for measurement of pulmonary arterial pressure, a balloon tube 6, a thermistor tube 12 and an indicator liquid infusion tube 10, respectively, at the base end of the catheter, as shown in FIG. 1. The tubes 8, 6, 10 have connectors 7, 9, 11 at their aft ends, respectively.

The thermistor tube 12 has a flared aft end and internally accommodates two tubes communicating at the flared aft end portion with respective ones of first and second thermistor tubes 13, 14 having connectors 15, 16, respectively. The first and second thermistor tubes 13, 14 in turn sheath lead wires 22, 24 (FIG. 2) electrically connected at one end to the thermistors 1, 2, respectively, and at the other end to the connectors 15, 16, respectively.

Though the lead wires 22, 24 from the thermistors 1, 2 are arranged inside the thermistor lumen 21 in the embodiment of FIG. 2, it is permissible to arrange these lead wires in separate lumens, in which case the catheter would be composed of five lumens. Further, the tubes 13, 14 and connectors 15, 16 can be integrated, in which case the lead wires need not be separately arranged in the double-tube structure mentioned above. It is also possible to adopt a common connector instead of the two connectors 15, 16.

Figure 3:
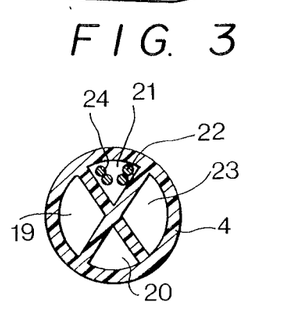
FIG. 3 is a sectional view taken along line III-III' of the embodiment of FIG. 2.

The catheter embodied in FIGS. 1 and 2 will now be described in greater detail. In the enlarged sectional view of FIG. 2, the portions at which the thermistors 1, 2 and balloon 17 are attached are clearly shown. Further, FIG. 3 is a sectional view of the catheter tube 4 taken along line III—III' The four lumens constituting the catheter 4, namely the balloon lumen 20, pulmonary arterial pressure lumen 19, infusion lumen 23 and thermistor lumen 21 are arranged as shown in FIG. 3. The balloon lumen 20 has the hole 25 inside the balloon and is thereby brought into communication with the balloon tube 6. The pulmonary arterial pressure lumen 19 has the pressure sensing port 18 at its tip and is thereby brought into communication with the pulmonary arterial pressure tube 8. The infusion lumen 23 has the discharge port 3 at a position 12–40 cm from the tip of the catheter, and is thereby brought into communication with the indicator liquid infusion tube 10 at the base end. The thermistor lumen 21 has holes 26, 27, in which the respective thermistors 1, 2 are mounted. The hole 26 is located 10–20 mm from the tip of the catheter, and the hole 27 is located 10–15 mm from the hole 26 on the base end side. The thermistor lumen 21 internally accommodates the lead wires 22, 24 from the thermistors 1, 2 and communicates at its aft end with the thermistor tube 12 and with the first and second thermistor tubes 13, 14.

It is preferred that the thermistor 1 be of the self-heating type, and that it be positioned downstream of the thermistor 2 in terms of the direction of blood flow. More specifically, if cardiac output is to be measured by the present catheter, it is required that the temperature of the diluted blood be measured accurately by the thermistor 2. For this reason, the thermistor 2 should he located upstream of the thermistor 1, where it will not be influenced by the heat from the thermistor 1.

As far as manufacturing the catheter is concerned, the first step is to fabricate, by extrusion molding, a tube having the four-lumen structure and a sectional shape of the type shown in FIG. 3. As illustrated in FIG. 1, the catheter tube accommodating these four lumens has a large inner diameter at a connector portion. The inner diameter of each lumen at the connection portion is enlarged in order to facilitate the insertion of the balloon tube 6, pulmonary arterial pressure measurement tube 8, indicator liquid infusion tube 10 and thermistor tube 12 into the corresponding lumens. This large-diameter portion is protected by a manifold connector 5. The large-diameter portion is formed by varying the resin discharge rate, drawdown speed and bore pressure during the extrusion molding process. The large-diameter portion is formed as a continuation of the catheter tube and is cut off from the immediately adjacent tube at a point that will provide the proper catheter length.

As for the tip portion of the catheter, the open end of the pulmonary arterial pressure lumen 19 is left open to form the pressure sensing port 18. The other lumens 20, 21, 23 have their tip portions closed off. It is particularly preferred that these lumens 20, 21, 23 be closed off in advance with a thermoplastic resin or filler such as polyurethane, poly-vinyl chloride, EVA, polyurethane or polypropylene. A material such as EVA is ideal as it fuses at a comparatively low temperature and can therefore be worked with ease.

The formation of the balloon 17 will be described below. The catheter is provided with the hole 25 communicating with the interior of the balloon. Next, a sleeve-shaped member 17 comprising latex rubber, polyurethane elastomer, synthetic rubber or silicone rubber is set so as to cover the vicinity of the catheter tip, and so that a portion thereof extends beyond the tip. This member serves as the balloon 17. The member 17 is affixed as by bonding to the catheter tip portion at a position 40 in FIG. 2. Thereafter, the leading edge of the member 17 is folded back so as to form a balloon. This edge is hermetically affixed to the catheter at a position 41 located further from the tip portion than the position 40. When the balloon 17 is inflated, as shown in FIG. 2, the distal end thereof extends beyond the catheter tip. This is desirable in that the tip of the catheter will not harm the blood vessel wall when the catheter travels through the vessel.

Figure 4:
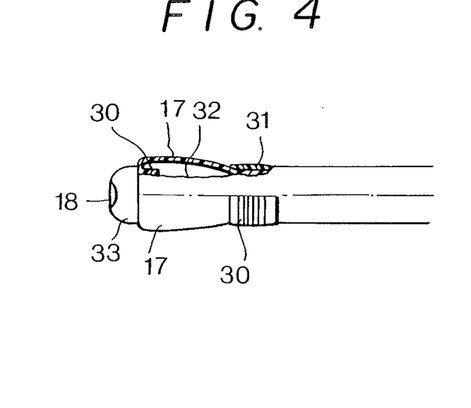
FIG. 4 is an enlarged perspective view, a portion of which is cut away, showing a balloon included in the arrangement of FIG. 2.

The balloon (the sleeve-shaped member) can be secured to the catheter tube by using a polyurethane, expoxy, cyanoacrylate or rubber bonding agent. Alternatively, however, the balloon can be affixed more reliably by applying windings of a nylon monofilament having a denier of 10–50, as shown in FIG. 4. If the sleeve-shaped member is adhered to the catheter tube by means of the bonding agent, it is permissible to apply the windings of the monofilament thereon. It is also permissible to melt the member to be secured on the tube by a melt molding process in which heat is generated ultrasonically or by application of high-frequency energy.. If a monofilament securing the balloon to the catheter at the position 41 is coated from above with polyurethane 31 or the like, as shown in FIG. 4, a smoother finish can be obtained. The outer diameter of the catheter tip after the balloon has been attached should be approximately the same as that of the catheter tube. Therefore, it is preferred that the catheter tip portion to which the balloon is attached be provided with a small-diameter portion 32, shown in FIG. 4, which can be formed by a heat treatment.

The method in which the catheter is used, though obvious to those skilled in the art, will now be described. The catheter 4 is inserted from an arm or leg vein and the tip thereof is positioned in the pulmonary artery. The location is verified based on the pressure and its waveform sensed from the pressure sensing port 18. After the catheter 4 has been properly emplaced, the pressure of the blood flowing into the pulmonary artery is measured. Next, the balloon 17 is inflated to block the pulmonary artery so that the pulmonary arterial wedge pressure can be determined. The pressure sensing port 18 is not only useful in monitoring pressure and waveform but can also be utilized as a port for administering medication. In such case the two thermistors 1, 2 of the catheter embodied herein function as useful sensing elements.

As for the characteristics of thermistor 1 used in the catheter of the illustrated embodiment, $B_{25-45}=3500$ $K$, $R(37)=1000\Omega$, and the thermistor has a size of $1.18^l 0.4^w \times 0.15^t$ (in millimeter units). The characteristics of the thermistor 2 are as follows: $B_{25-45}=2980$ $K$, $R(37)=40$ $K\Omega$, and the thermistor has a size of $0.50^l \times 0.16^w \times 0.15^t$. It is preferred that the thermistor 1 produce heat having a calorific value of 0.01–50 J. A higher calorific value is undesirable as will raise the temperature of the blood or cause the damage of blood vessel wall, while a lower calorific value is disadvantageous in that it will result in a detection sensitivity which is too small.

These thermistors are set up as shown in FIG. 2. Polyurethane, a cyanoacrylate bonding agent, epoxy or a UV-curable bonding agent is ideal for both fixing and insulating the thermistors. When the thermistors are fixedly mounted in the holes 26, 27 of the lumen 21, the interior of the lumen 21 should be sealed at the front and back of each hole 26, 27 by a PVC monofilament or adhesive to prevent any bonding agent from flowing into the lumen.

By using the above-described technique, the thermistor 1 is secured at a position 20 mm from the tip of the catheter, and the thermistor 2 is secured at a position 10 mm from the thermistor 1 on the side thereof closer to the base end of the catheter. The lead wires of these thermistors are passed through the lumen 21, the thermistor tubes 12, 13, 14 and are finally connected to the connectors 15, 16.

The thermistor lumen 21 is thus connected to the connectors 15, 16. The other lumens are connected to the other connectors 7, 9, 11 in a well-known manner via the manifold connector 5. The pulmonary arterial pressure measurement tube 8 and connector 9 are connected to the pulmonary arterial pressure lumen 19, the balloon tube 6 and balloon connector 7 are connected to the balloon lumen 20, and the indicator liquid infusion tube 10 and infusion connector 11 are connected to the indicator liquid infusion lumen 23.

The apertures of the infusion lumen 23 are 5 Fr (french size) 15 cm from the tip and 7 Fr 30 cm from the tip (the usual values being 4–8 Fr, 12–40 cm). The portion of the infusion lumen from the discharge port 3 to the tip is sealed with a bonding agent similar to that used to fix the thermistors.

In order to indicate the inserted distance, the cathether is suitably marked by ring like marks at distances of 10, 20, 30, 40, 50, 60, 70, 80, 90 and 100 cm from the tip thereof.

This completes the discussion of catheter fabrication.

Figure 7:
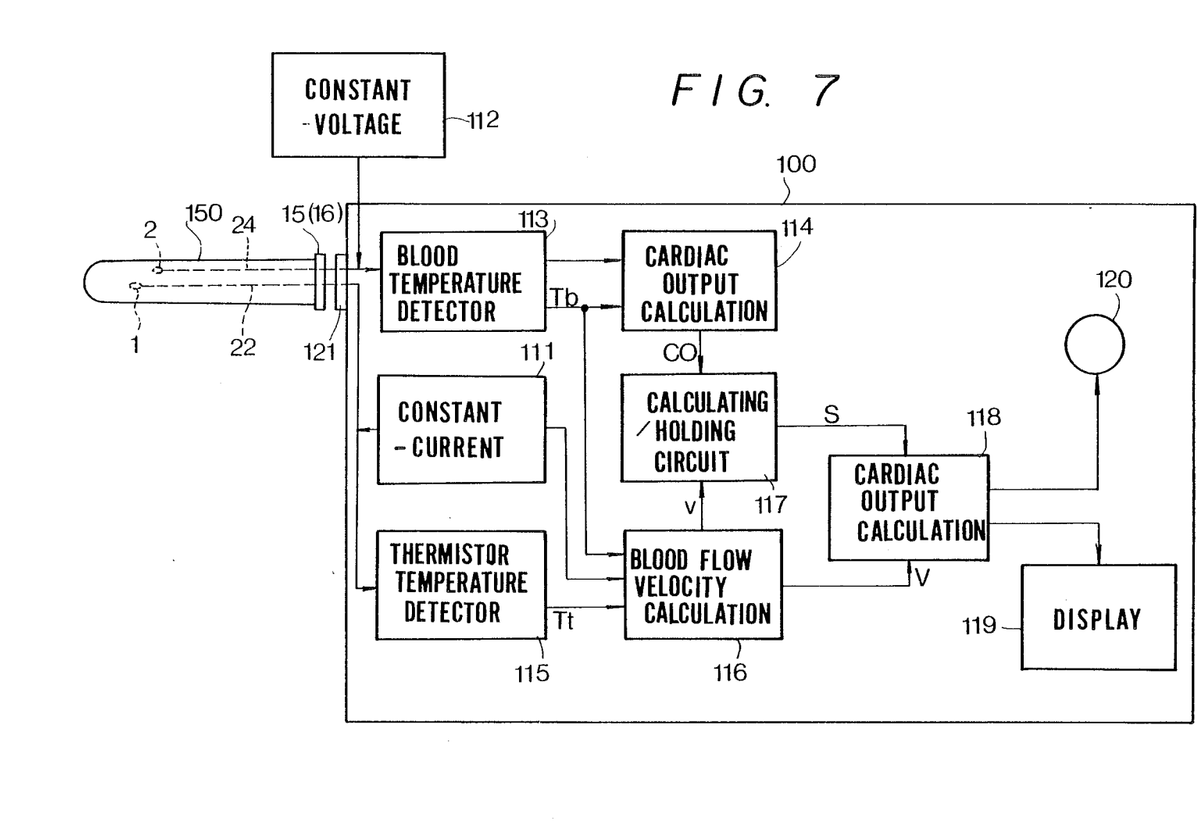
FIG. 7 is a block diagram illustrating an embodiment of a cardiac output measurement system to which a catheter in accordance with the illustrated embodiment is connected.

Though the catheter described herein is used upon being connected to a system for continuously measuring cardiac output or blood flow velocity, it goes without saying that the catheter is employed in the same way as an ordinary thermodilution catheter. When the inventive catheter for cardiac output measurement is connected to a system for measuring cardiac output, the thermistor connector 16 is connected to the system in accordance with the ordinary thermodilution method, as shown in FIG. 7. To measure cardiac output continuously, the thermistor connector 15 is connected to a system for continuous measurement of cardiac output. The principle of such a continuous measurement system is disclosed in the specification of Japanese Patent Application No. 59-244586 (filed on Nov. 21, 1984 and laid open on June 13, 1986 as Japanese Patent Application Laid-Open No. 61-125329). This system will now be described.

FIG. 7 is a block diagram of a measurement system for continuously measuring cardiac output. The system includes a cardiac output measurement unit 100 which employs the catheter 4 of the above-described embodiment as a catheter-type sensor 150.

The catheter-type sensor 150 incorporates the self-heating thermistor 1 and the thermistor 2, which serves as a temperature-sensitive element for sensing the temperature of blood within the pulmonary artery. The thermistor 1 is heated by a constant current from a constant-current circuit 111 and is adapted to sense its own temperature. The thermistor 1, which is arranged to function as a sensing element, is not limited to a self-heating type thermistor. It is permissible to make use of an ordinary thermistor heated by being provided near a separate heater that produces a constant amount of heat. However, self-heating thermistor of the kind embodied in FIGS. 1 and 7 is preferred structurally because it is easy to incorporate and functionally because of its stable heat generating and sensing properties.

The catheter-type sensor 150 is introduced into the pulmonary artery by the right heart catheter method through a conventional technique similar to that described above. The connector 15 (16) of the sensor 150 is joined to a connector 121 of the measuring unit 100. The thermistor 2 is connected to a constant-voltage circuit 120, which is for driving the thermistor 2, and to a blood temperature sensing circuit 113 for measuring blood temperature. The constant-current circuit 111 may be used instead of the constant-voltage circuit 120. A signal produced by the thermistor 2 indicative of pulmonary artery blood temperature is applied to the blood temperature sensing circuit 113, where the signal is detected and delivered as a temperature signal suitable for signal processing.

The blood temperature detecting circuit 113 is connected to a thermodilution-type cardiac output calculating circuit 114 for applying the blood temperature signal thereto. Upon receiving the blood temperature signal, and using Eq. (1), the calculating circuit 114 calculates cardiac output from the area of the dilution curve (FIG. 6) by the thermodilution method in accordance with the Stewart-Hamilton process.

The thermistor 1 incorporated in catheter-type sensor 150 is connected to a thermistor heating/temperature sensing circuit 115 and the constant-current circuit 111 via the lead wire 22. When necessary, the constant-current circuit 111 supplies the thermistor 1 with a prescribed current to heat the same. A heating/temperature signal sensed by the thermistor 1 is applied to the thermistor heating/temperature sensing circuit 115. Here the signal is detected as the thermistor resistance value $R_t$ or potential difference $V_0$, and the temperature signal $T_t$. The thermistor heating/temperature sensing circuit 115 and the blood temperature sensing circuit 113 are connected to a blood flow velocity calculating circuit 116, which calculates the blood flow velocity v based on the temperature signal $T_t$ and thermistor resistance value $R_t$ or potential difference V Let us now describe the principle and method of calculating blood flow velocity v as performed by the blood flow velocity calculating circuit 116. Let $R_t$ represent the resistance value of the thermistor 1, and let $I_c$ denote the magnitude of the current applied to this thermistor 1 by the constant-current circuit 111. When the thermistor 1 is heated, the quantity of heat generated per unit time will be $I_c^2 \cdot R_t$.

When the heated thermistor 1 is placed in blood flowing at a velocity v, the thermistor 1 is cooled to an extent dependent upon the blood flow velocity v. The quantity of heat lost by such cooling is expressed by $K \cdot v \cdot (T_t - T_b)$, where $T_b$ is the blood temperature, $T_t$ is the temperature of the heated thermistor, and K is a constant of proportion. The thermistor 1 is maintained at a temperature which will establish equivalence between the quantity of heat generated and the quantity of heat taken away by cooling. This temperature is the equilibrium temperature. Expressing the foregoing by an equation, we have $$I_c^2 \cdot R_t = K \cdot v \cdot (T_t - T_b) \qquad (2)$$

The following equation for finding blood flow velocity v is derived from Eq. (2):

$$v = (1/K) \cdot (I_c^2 \cdot R_t)/(T_t - T_b) \qquad (3)$$

Since the heated thermistor is driven by the constant-current circuit 111, the potential difference $V_0$ across the ends of the lead wire of the heated thermistor 1 may be detected as an alternative to detecting the resistance value $R_t$. In such case, $V_0$ is equal to $R_t I_c$, so that Eq. (3) may be rewritten as follows:

$$V = (1K) \cdot (I_c \cdot V_0)/(T_t - T_6) \qquad (3+)$$

It will be obvious from Eq. (3) or (3') that the blood flow velocity v may be obtained from the resistance value $R_t$, or the potential difference $V_0$, of the heated thermistor 1, taken together with the temperature $T_t$ of the heated thermistor 1, the current value $I_c$, the blood temperature $T_b$ found by the thermistor 2, and the proportional constant K. The thermistor heating/temperature sensing circuit 115 provides the blood flow velocity calculating circuit 116 with the resistance value $R_t$ (or potential difference $V_0$) and temperature $T_t$. The blood temperature sensing circuit 113 applies the blood temperature $T_b$ to the blood flow velocity sensing circuit 116. The latter calculates the blood flow velocity v in accordance with Eq. (3) or (3') based on the information received.

Noted that though the constant-current value $I_c$ can be obtained by detecting the current of the constant-current circuit 111, it is also possible to provide the blood flow velocity calculating circuit 116 with $I_c$ in the form of a constant term, as in the manner of the constant of proportion K.

The blood flow velocity calculating circuit 116 and the thermodilution-type cardiac output measuring circuit 114 are connected to a calculating/holding circuit 117 for calculating and holding a parameter, described below. The calculating/holding circuit 117 comprises an arithmetic circuit for calculating blood vessel cross-sectional area, and a sample-and-hold circuit for holding, as a parameter, the blood vessel cross-sectional area value calculated by the arithmetic circuit. More specifically, the circuit 117 functions to calculate a parameter S, on the basis of Eq. (4) given hereinbelow, from a cardiac output value CO, calculated by the thermodilution-type cardiac output measuring circuit 114 in accordance with the thermodilution method, and the blood flow velocity v value obtained from the blood flow velocity calculating circuit 116.

Let S represent the blood vessel cross-sectional area of the pulmonary artery. The cardiac output value CO and blood flow velocity value v are related as follows:

$$CO = S \cdot v \qquad (4)$$

The calculating/holding circuit 117 determines the blood vessel cross-sectional area S in accordance with Eq. (4) from the cardiac output value CO and the blood flow velocity value v, and holds the value S as a calibration value (parameter). When the parameter S has thus been obtained, a cardiac output calculating circuit 118 multiplies the blood flow velocity v, which is continuously measured by the blood flow velocity calculating circuit 116, by the parameter S held in calculating/holding circuit 117, thereby making it possible to obtain a cardiac output value CO that is continuous.

The cardiac output calculating circuit 118 is connected to a display unit 119 and recorder output terminal 120 so that the cardiac output obtained may be continuously displayed and recorded. It should be noted that instead of treating S as a parameter, the following Eq. (5) can be derived from Eqs. (3), (4), and "S/K" in Eq. (5) can be held as a parameter:

$$C = (S/K) \cdot (I_c^2 \cdot R_t)/(T_t - T_b) = (S/K) \cdot (I_c \cdot V_0)/(T_t - T_b) \qquad (5)$$

The parameter S representing the blood vessel cross-sectional area varies with time; hence, even though S is held as a calibration value in the calculating/holding circuit 117, the change in blood vessel cross-sectional area S can make it difficult to obtain an accurate cardiac output. To overcome this problem, it is possible to carry out control in such a manner that cardiac output CO is measured by the cardiac output calculating circuit 114 in accordance with the thermodilution method,: a new value of the blood vessel cross-sectional area S is obtained by the calculating/holding circuit 117 in accordance with Eq. (4), and this value is held as the new parameter. In actuality, a routine for updating this parameter is executed by the measurement system as part of the control operation performed thereby.

The thermodilution-type cardiac output calculating circuit 114, thermistor heating/temperature sensing 115, blood flow velocity calculating circuit 116, holding circuit 117 and cardiac output calculating circuit 118 may be advantageously constituted by a microcomputer comprising a one-chip LSI. In such case, the entire control sequence would be stored in an internal memory. In addition, the blood temperature detecting circuit 113 and thermistor heating/temperature sensing circuit 115 would both be realized by analog-digital converters and these would also be incorporated in the one-chip microcomputer.

Figure 8:
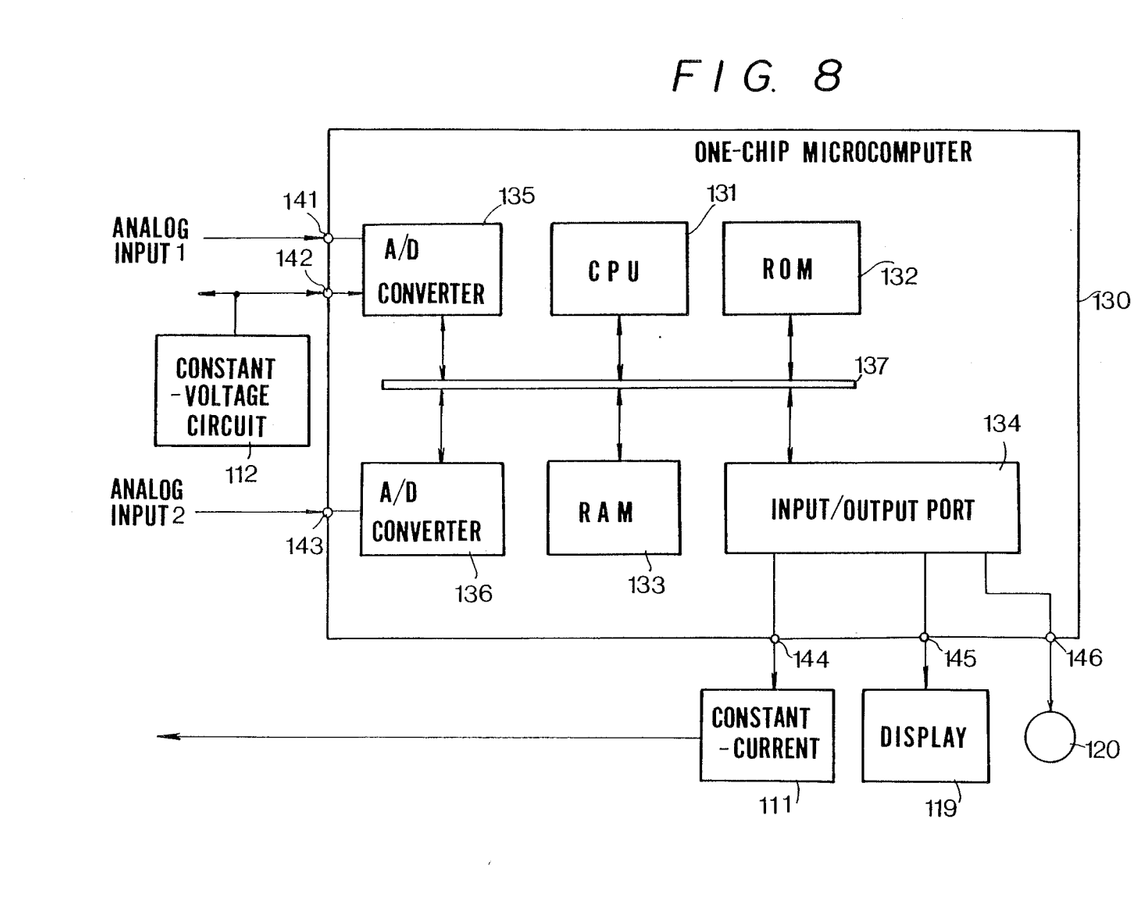
FIG. 8 is a view showing the arrangement of a one-chip microcomputer constituting a portion of the cardiac output measurement system of FIG. 7.

FIG. 8 is a block diagram of a one-chip microcomputer for executing the above-described functions. More specifically, in FIG. 8, the sections 114–118 shown in block form in FIG. 7 are represented as function blocks implemented by the above-described microcomputer.

A CPU 131 executes various processing in accordance with a program (FIG. 10) stored in a ROM 132. The results of processing are stored in a RAM 133. An input/output port 134 includes an output terminal 144 for controlling the ON/OFF operation of the constant-current circuit 111, an output terminal 145 for controlling the display of information on the display unit 119, and an output terminal 146 connected to the recorder 120. Analog-digital converters 135, 136, taken together with bridge circuits, not shown, correspond to the blood temperature sensing circuit 113 and thermistor heating/temperature sensing circuit 114 (FIG. 7), respectively. These A/D converters 135, 136 receive analog signals at respective analog input terminals 141, 143 and convert these signals into digital signals for processing by the CPU 131.

Figure 9:
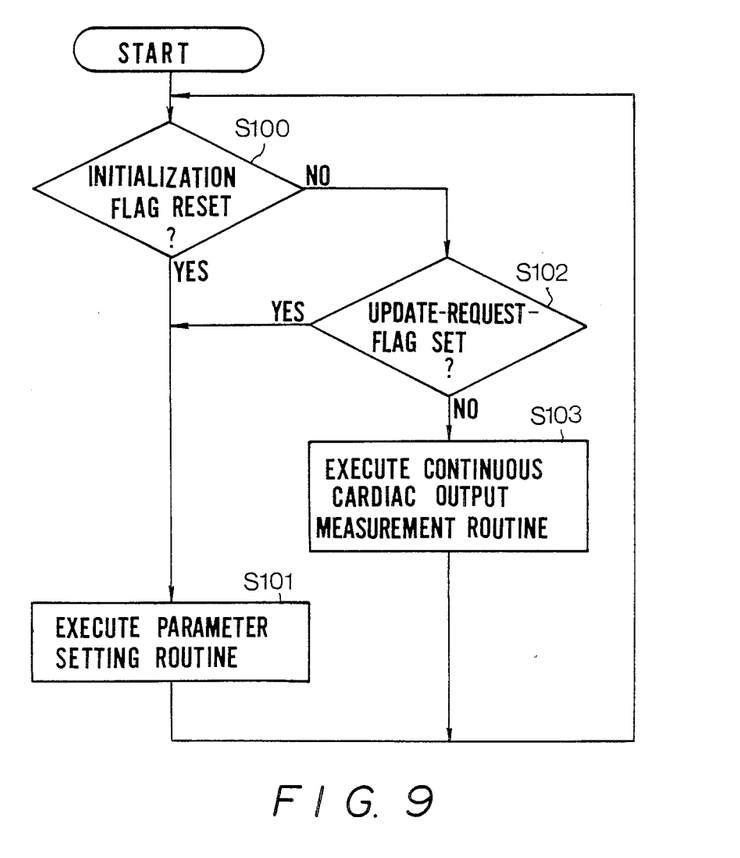
FIGS. 9, 10(A), (B) and 11 are control flowcharts associated with the cardiac output measurement system of FIG. 7.
Figure 10A:
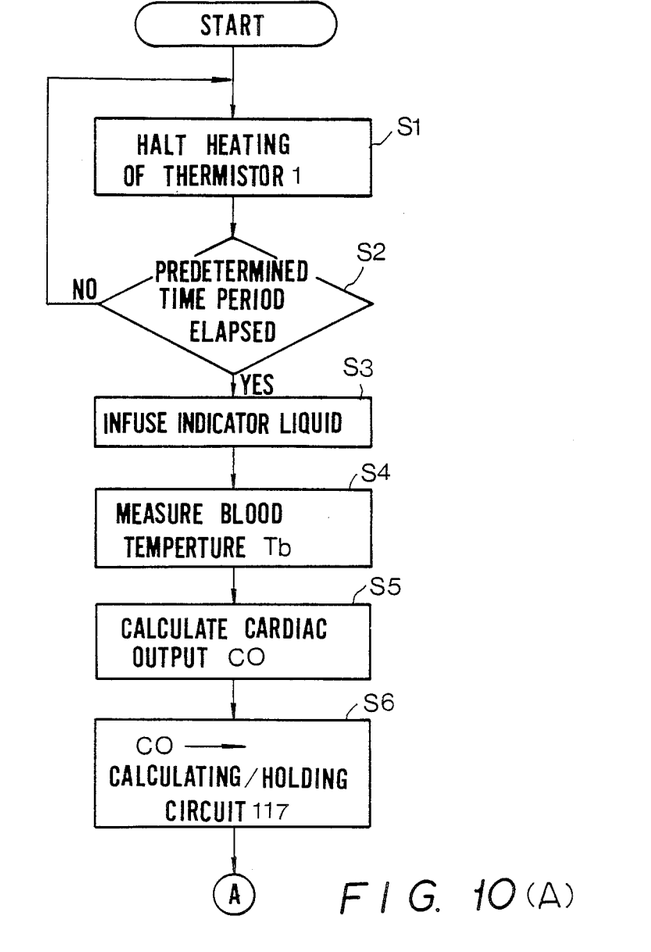
Figure 10B:
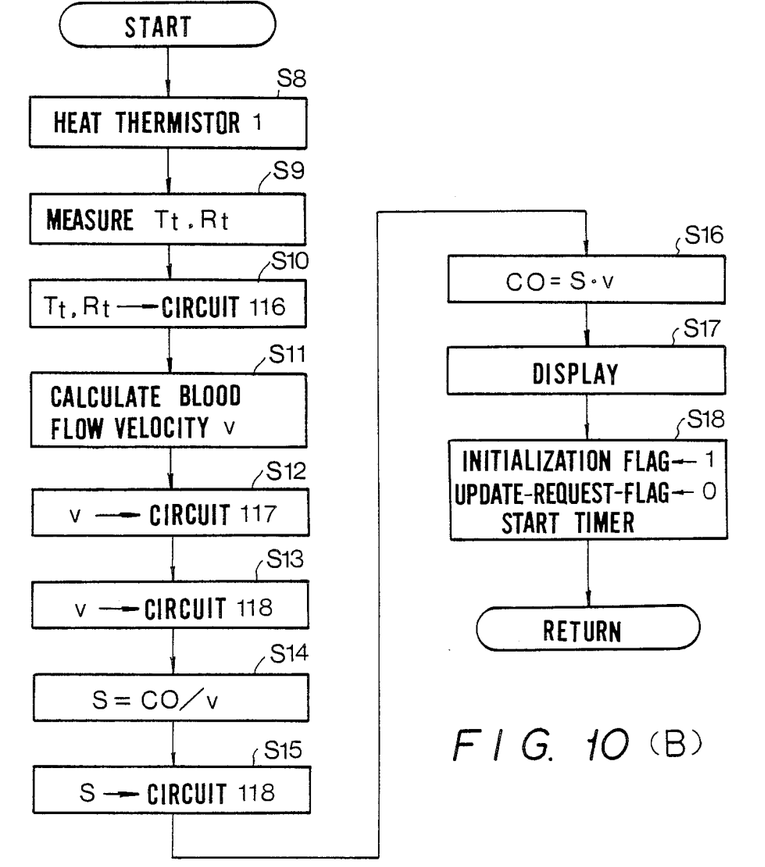
Figure 11:
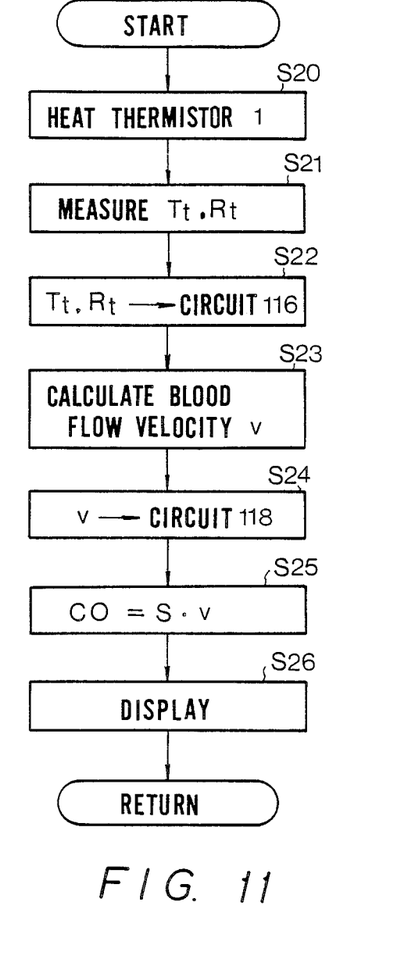

Let us now turn to the flowcharts of FIGS. 9, 10, 11 to describe the details of a control procedure which the CPU 131 executes in accordance with a processing program stored in ROM 132. This will serve as a specific example of a cardiac output measurement operation performed by the cardiac output measurement system of the present embodiment.

The flowchart of FIG. 9 shows a main routine relating to control executed by the cardiac output measurement system to which the catheter of the present invention is applied. The functions implemented include deciding the necessity of initially setting the abovementioned parameter S (blood vessel cross-sectional area) in the calculating/holding circuit 117 or of updating the parameter (steps S100, S102), and, in accordance with the decision rendered, setting the parameter S in the calculating/holding circuit 117 (step S101) and continuously measuring cardiac output (step S103).

When control in accordance with the flowchart of FIG. 9 starts, it is determined at step S100 whether the parameter S is to be initially set. If a YES decision is rendered, then the parameter setting routine of step S101 is executed. Setting the initial value of the parameter is performed when the cardiac output of a patient is measured the first time, when the system is turned on, etc., and is supervised by an initialization flag in RAM 133. The parameter setting routine entails measuring cardiac output based on the thermodilution method, sensing blood flow velocity, calculating the parameter S and holding the calculated parameter in the holding circuit 117. The details of the parameter setting routine are shown in FIG. 10. In accordance with this routine, the abovementioned flag indicating that the initial value has been set is raised, after which the program returns to step S100, as will be apparent from the flowchart described below.

When the program returns to the step S100, it is found that the aforementioned flag has been set. Therefore, a NO decision is rendered and the program proceeds to step S102, at which it is determined whether it is necessary to update the held value of the parameter. Whether or not updating is necessary is determined by investigating an update request flag, the setting of which is controlled in the following manner: A clinically decided time at which it becomes necessary to update the parameter is previously set in a timer (not shown) within the microcomputer 130. When the set time expires, the update request flag is set by a timer interrupt routine (not shown). When the update request flag has been set, a YES decision is rendered at step S102, so that the parameter setting routine (an updating routine in this case) of step S101 is executed When the parameter has been updated, the update request flag is reset and the timer is restarted in the setting routine.

If a NO answer is received at step S102, this means that the parameter S is valid and reliable. Accordingly, a measurement routine (step S103) for continuously measuring cardiac output is executed The details of the measurement routine are shown in FIG. 11.

It should be noted that an arrangement may be adopted in which the update request flag can be set by an externally provided switch It is preferred that the parameter setting routine not be executed automatically when the update request is generated. Instead, when the request is generated, the operator's attention should be called and the parameter setting routine executed again only after the operator confirms that it is permissible for the thermodilution method to be performed again. The purpose of this is to assure the patient's safety.

The details of the parameter setting routine (step S101 of FIG. 9) will now be described with reference to FIG. 10(A). When the program proceeds to step S1 of the flowchart shown in Fig. 10(A), this will mean that the initial value setting: flag has been reset or that the update request flag has been set. In other words, step S1 is reached when either of these two conditions is satisfied. This step calls for heating of the thermistor 1 to be suspended. The program then proceeds to step S2 and waits for passage of a prescribed period of time to allow sufficient cooling of thermistor 1 so that thermistor 2 will no longer be influenced thereby When this time period elapses, the program proceeds to step S3, at which a fixed amount of indicator liquid is ejected from the discharge port 3 of catheter 4 (FIG. 1). Next, at step S4, the blood temperature sensing circuit 113 receives a signal from the thermistor 2 for measuring the temperature $T_b$ of the blood diluted by the indicator liquid. The circuit 113 outputs a signal indicative of $T_b$ to the thermodilution-type cardiac output calculating circuit 114. Upon receiving the temperature signal $T_b$, the calculating circuit 114 calculates the cardiac output CO from Eq. (1) at step S5. The calculated value of cardiac output CO is outputted to the calculating/holding circuit 117 at step S6. Thus, cardiac output CO is measured in accordance with the thermodilution method.

In FIG. 10(B), the steps from S8 onward constitute a routine for obtaining blood flow velocity and setting the parameter S in the calculating/holding circuit 117. At step S8, the constant current circuit 11 is driven into operation to heat the thermistor 1 by applying a predetermined current $I_c$ thereto. Next, at step S9, the thermistor heating/temperature sensing circuit 115 senses the temperature $T_t$ of the heated thermistor 1 itself and the thermistor resistance value $R_t$ or potential difference $V_0$ and outputs these to the blood flow velocity calculating circuit 116 at step S10. The program then proceeds to step S11, at which the blood flow velocity calculating circuit 116 calculates the blood flow velocity v in accordance with Eq. (3) upon receiving the signals from the sensing circuit 115 indicative of the temperature $T_t$, resistance value $R_t$ or potential difference $V_0$ and the signal from the blood temperature sensing circuit 113 indicative of the blood temperature $T_b$. The calculated value of blood flow velocity v is then outputted to the calculating/holding circuit 117 at step S12, and to the cardiac output calculating circuit 118 at step S13.

This is followed by a step S14, at which the calculating/holding circuit 117 obtains, and holds as a parameter, the blood vessel cross-sectional area S in accordance with Eq. (4) by using the cardiac output CO from the thermodilution-type cardiac output calculating circuit 114 and the blood flow velocity v. The calculating/holding circuit 117 outputs this parameter value S to the cardiac output calculating circuit 118 at a step S15. The next step S16 calls for the cardiac output calculating circuit 118 to obtain the cardiac output CO from the blood flow velocity v and the parameter value S, which is received from the calculating/holding circuit 117, based on the equation CO=v S. The value of the cardiac output obtained is displayed by the display unit 119 and, when necessary, delivered to the output terminal 120.

This ends the setting of the parameter, whereupon the program returns to step S100 of the main routine.

The details of the continuous cardiac output measurement routine are shown in FIG. 11. When the program proceeds to this measurement routine, this will mean that the initial value setting flag has been set and, moreover, that the update request flag has been reset. In other words, step S20 is reached when the parameter S set in the calculating/holding circuit 117 is reliable. Steps S20 through S23 of the flowchart in FIG. 11 are the same as steps S8 through S11 of the flowchart in FIG. 11(B) and need not be described again here. Step S24 calls for the determined value of flow velocity v to be delivered to the cardiac output calculating circuit 118. The latter obtains the cardiac output CO at step S25 by multiplying the parameter S, held and outputted by the calculating/holding circuit 117, by the flow velocity v. The obtained value of cardiac output CO is displayed and outputted at step S26, after which the program returns to the main routine.

Thus, cardiac output CO can be measured merely by measuring the blood flow velocity v. Moreover, the cardiac output CO can be measured continuously, merely by measuring the blood flow velocity v, until the update request flag is set. In other words, the cardiac output measurement catheter in accordance with the above-described embodiment employs a continuous thermal-type flowrate measurement method based on heating of a sensing element, not an intermittent method as in a conventional cardiac output measurement that relies solely upon thermodilution. This makes it possible to provide a continuous cardiac output measurement signal. Furthermore, with the conventional thermodilution method, frequent measurement subjects the patient to a great burden due to the quantity of liquid infused. In accordance with the cardiac output measurement catheter of the invention, however, the abovementioned parameter for obtaining cardiac output is found with just a single infusion of liquid, after which continuous measurement can begin. This lightens the load on the patient, simplifies operation and reduces the risk of infection.

It will be appreciated from the foregoing description that this continuous cardiac output measurement is characterized in that once the cardiac output CO is measured by some appropriate method, the parameter S is measured based thereon, the value of the parameter S is held, and thenceforth cardiac output is obtained continuously merely by measuring blood flow velocity. Accordingly, the catheter of the present invention is not limited to an arrangement for obtaining an initial value of cardiac output CO through measurement based on the thermodilution method, as in the above-described embodiment, for the catheter can also be applied to an arrangement adapted to obtain an initial value of cardiac output CO by e.g. The dye dilution method, resistance value dilution method or the like. If the dye dilution method is used, the cardiac output CO is found by measuring a quantity of dye in the blood at e.g. The patient's earlobe. With the resistance value dilution method, the cardiac output CO is obtained by measuring the resistance value of the blood using two electrodes provided on the catheter. In either of these arrangements, the function of the thermistor 2 is to measure the blood temperature $T_b$ which prevails when the blood flow velocity v is obtained.

The catheter of the invention can also be used to determine the blood flow velocity alone. Two such arrangements are proposed, one in which only the thermistor 1 is employed, and another in which both of the thermistors 1, 2 are used, with the thermistor 2 constituting the load of the thermistor 1. With the single-thermistor catheter, the measurement error on the side of the cardiac output measurement unit 100 increases, and an absolute value cannot be obtained, since $T_b$ is not obtained in the process for determining the blood flow velocity. However, since there are cases where a change in the relative value of cardiac output is important in a cardiac output measurement system, the single-thermistor catheter is a valuable tool. In a case where the blood flow velocity measurement catheter having . the thermistor 2 loading the thermistor 1 is connected to the cardiac output measurement unit 100, a relative value of cardiac output may be obtained even though the parameter S is set on the side of the cardiac output measurement unit 100. Such an arrangement is particularly meaningful when ascertaining the change in cardiac output with time.

In another possible modification, measurement of blood flow velocity by the thermistor 1 can be achieved not only by sensing thermal equilibrium under a condition of constant current, namely a change in the resistance of the thermistor, in the form of voltage or the like, but also by passing a current necessary to render a temperature differential with the blood temperature constant and measuring this current. In other words, this method entails controlling the thermistor temperature to an upper limit of 42° C., which will not affect a living body, and measuring the current that prevails at such time. It should also be noted that the blood flow velocity sensor is not limited to a thermistor; other means may be employed for such purpose.

As many apparently widely different embodiments of the present invention can be made without departing from the spirit and scope thereof, it is to be understood that the invention is not limited to the specific embodiments thereof except as defined in the appended claims.

What we claim is:

1. A catheter connected to an apparatus for continuously measuring cardiac output based on a cardiac output value initially measured by using a dilution method, values of a continuously measured blood flow velocity signal and a relationship between the cardiac output value initially measured and blood flow velocity, said catheter comprising:
    an aperture portion for discharging a liquid for measuring the cardiac output based on the thermodilution method;
    temperature sensing means, including a temperature sensing element arranged at a predetermined distance from said aperture portion, for sensing the temperature of blood diluted by the liquid; and
    a self-heating type thermistor, located at a distance of five to twenty-five millimeters from said temperature sensing means and having a calorific value of 0.01 to 50 joules with a direct relation between the distance and the calorific value, for sensing an equilibrium temperature resulting from a quantity of heat applied thereby and a quantity of heat absorbed by the blood.

2. The catheter according to claim 1, wherein said temperature sensing element is provided on a side of said aperture portion toward a tip end of the catheter.

3. The catheter according to claim 1, wherein said temperature sensing element is provided on a side of said aperture portion toward a base end of the catheter.

4. The catheter according to claim 1, wherein said catheter has an interior partitioned into at least two independent lumens, one of said lumens communicates with said aperture portion and the other of said lumens is closed at a tip portion of said catheter, lead wires of said temperature sensing element and said thermistor being passed therethrough.

5. The catheter according to claim 1, further comprising a pressure port used for sensing pressure.

* * * * *

UNITED STATES PATENT AND TRADEMARK OFFICE
CERTIFICATE OF CORRECTION

PATENT NO. : 4,841,981

DATED : June 27, 1989

INVENTOR(S) : Tanabe et al.

It is certified that error appears in the above-identified patent and that said Letters Patent is hereby corrected as shown below:

Col. 7, line 10, "$1.18^1 0.4^w$" should be --$1.18^1 \times 0.4^w$--.

line 11, "2980" should be --3980--.

Col. 8, line 66, "V" should be --$V_0$.--.

Col. 9, line 6, "/" should be -- · --;

line 33, "V" (first occurrence) should be --v--; "$T_6$" should be --$T_b$--; "(3+)" should be --(3')--;

Col. 12, line 24, "thereby" should be --thereby.--;

Col. 13, line 63, "The" should be --the--;

line 66, "The" should be --the--;

Col. 14, line 21, delete ".".

Signed and Sealed this

Seventeenth Day of April, 1990

Attest:

HARRY F. MANBECK, JR.

*Attesting Officer*  *Commissioner of Patents and Trademarks*